United States Patent [19]

Schaub et al.

[11] 4,046,787

[45] Sept. 6, 1977

[54] NOVEL 15-SUBSTITUTED PROSTANOIC ACIDS AND ESTERS

[75] Inventors: Robert Eugene Schaub, Upper Saddle River; Martin Joseph Weiss, Oradell, both of N.J.

[73] Assignee: American Cyanamid Company, Stamford, Conn.

[21] Appl. No.: 625,406

[22] Filed: Oct. 24, 1975

Related U.S. Application Data

[62] Division of Ser. No. 468,795, May 9, 1974, Pat. No. 3,932,472, which is a division of Ser. No. 274,558, July 24, 1972, Pat. No. 3,835,179.

[51] Int. Cl.[2] .......................................... C07C 177/00

[52] U.S. Cl. ............................... 260/399; 260/455 R; 260/514 D; 560/121

[58] Field of Search .......... 260/455 R, 468 D, 514 D, 260/399

[56] References Cited

PUBLICATIONS

Burger, Medicinal Chemistry, p. 77 (1960).

*Primary Examiner*—Robert Gerstl
*Attorney, Agent, or Firm*—Denis A. Polyn

[57] ABSTRACT

This disclosure describes compounds of the class of 15-substituted-9-keto(or 9-hydroxy)prostanoic acids and the esters and cationic salts thereof, useful as inhibitors of gastric acid secretion.

16 Claims, No Drawings

NOVEL 15-SUBSTITUTED PROSTANOIC ACIDS AND ESTERS

CROSS REFERENCE TO RELATED APPLICATIONS

This application is a division of our copending application Ser. No. 468,795, filed May 9, 1974, now U.S. Pat. No. 3,932,472 which is a division of our application Ser. No. 274,558, filed July 24, 1972, now U.S. Pat. No. 3,835,179.

BRIEF SUMMARY OF THE INVENTION

This invention relates to novel organic compounds related to the prostaglandin hormones. In particular, the compounds of this invention are 15-substituted-9-keto(or 9-hydroxy)prostanoic acids, their derivatives and congeners, and certain intermediates for the preparation of same. These compounds may be represented by the following general formula:

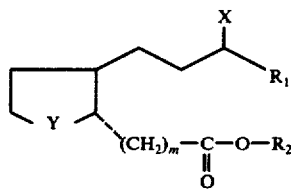

wherein $R_1$ is an alkyl group having from 2 to 7 carbon atoms; $R_2$ is selected from the group consisting of hydrogen and an alkyl group having from 1 to 12 carbon atoms; X is selected from the group consisting of lower alkylsulfonyloxy, halogen, lower alkanoylthio, mercapto, thiocyano, azido and amino radicals; $m$ is an integer with the value 3 to 9 and Y is a divalent radical selected from the group consisting of

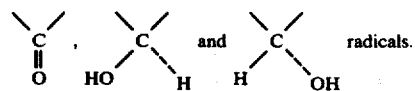

Suitable lower alkyl and lower alkanoyl groups contemplated by the present invention are those having up to four carbon atoms such as methyl, ethyl, isopropyl, sec-butyl, formyl, acetyl, isobutyryl, etc. Halogen is exemplified by chloro, bromo, and iodo.

Also embraced within the scope of the present invention are the non-toxic, pharmaceutically acceptable salts of the 15-substituted-9-oxo(or hydroxy)prostanoic acids when $R_2$ is hydrogen in the above general formula. The cations comprised in these salts include, for example, the non-toxic metal cations such as the sodium ion, potassium ion, calcium ion, and magnesium ion as well as the organic amine cations such as the tri(lower alkyl)amine cations (e.g., triethylamine), procaine, and the like.

The novel 15-substituted-9-oxo(or 9-hydroxy)prostanoic acids and esters thereof of the present invention are obtainable as yellow oils having characteristic absorption spectra. They are relatively insoluble in water but are relatively soluble in common organic solvents such as ethanol, ethyl acetate, dimethylformamide, and the like. The cationic salts of the 15-substituted-9-oxo(or 9-hydroxy)prostanoic acids are, in general, white to yellow crystalline solids having characteristic melting points and absorption spectra. They are relatively soluble in water, methanol, and ethanol but are relatively insoluble in benzene, diethyl ether, and petroleum ether.

DETAILED DESCRIPTION OF THE INVENTION

The prostaglandins are a family of closely related compounds which have been obtained from various animal tissues, and which stimulate smooth muscle, lower arterial blood pressure, antagonize epinephrine-induced mobilization of free fatty acids, and have other pharmacological and autopharmacological effects in mammals. See Bergstrom et al., J. Biol. Chem. 238, 3555 (1963) and Horton, Experientia 21, 113 (1965) and references cited therein. All of the so-called natural prostaglandins are derivatives of prostanoic acid:

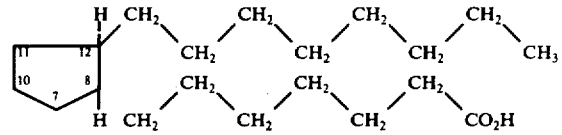

The hydrogen atoms attached to C-8 and C-12 are in trans configuration.

The novel compounds of this invention are prepared in accordance with the following reaction scheme:

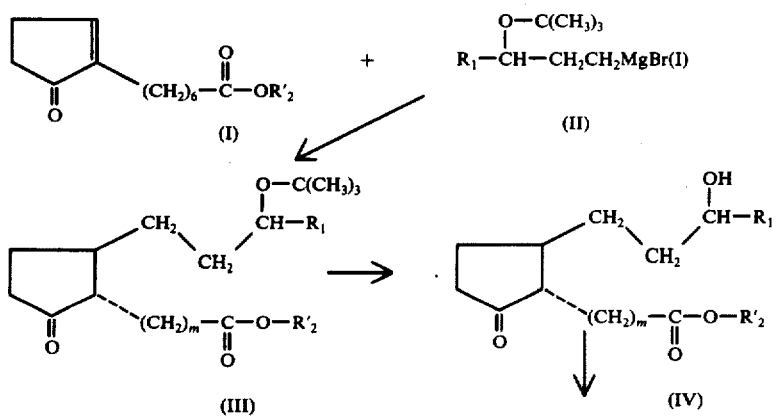

-continued

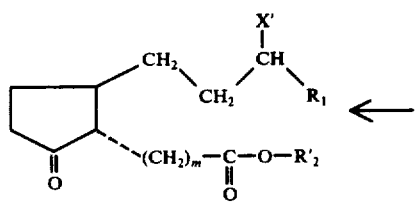

(VI)

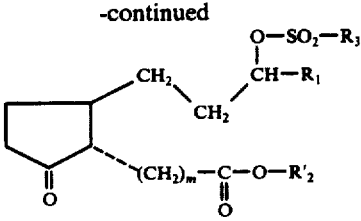

(V)

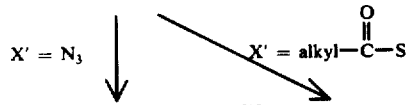

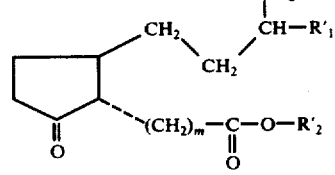

(VII)

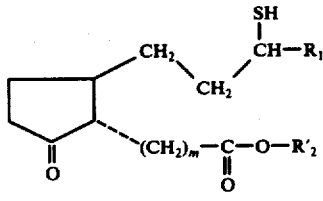

(VIII)

wherein $R_1$ and $m$ as hereinbefore defined, $R'_2$ is an alkyl group having from 1 to 12 carbon atoms, preferably methyl or ethyl, $R_3$ is a lower alkyl group, X' is selected from the group consisting of halogen, lower alkanoylthio, and azido radicals.

In accordance with the above reaction scheme, the conjugate 1,4-addition of a 3-(substituted hydroxy)alkyl magnesium halide (II) to an alkyl ester (I) of 2-(ω-carboxyalkyl)cyclopent-2-en-1-one is carried out in the presence of a catalyst such as the tributylphosphine-cuprous iodide complex; $(C_4H_9)_3P \cdot CuI$. This reaction is best carried out in the usual way in an ether-type solvent such as diethyl ether, dibutyl ether, tetrahydrofuran, and the like, at room temperature for a period of time of from two to eighteen hours. The intermediate magnesium halide-enolate adduct is then hydrolyzed in situ, preferably with ammonium chloride, at room temperature and the product (III) is isolated in the usual manner well known in the art.

Removal of the O-t-butyl blocking group from (III) to afford (IV) is conveniently effected by treatment with glacial trifluoroacetic acid at from −5° to 10° C. for a period of one to three hours. Since this procedure may lead to partial trifluoroacetylation of the free hydroxy function, it is preferably followed by treatment with aqueous ammonia (about 1.0N concentration) for about 15 minutes at ambient temperatures. In order to ensure the formation of the depicted trans relationship between the two side-chains, the product can be further treated under alkaline or acidic conditions known to promote equilibration to the thermodynamically-favored transrelationship. Such conditions include treatment with potassium acetate in aqueous methanol for 96 hours at room temperature.

For the introduction of the various groups embraced by the above definition of X the 15-hydroxy derivative (IV) is converted to the corresponding 15-alkylsulfonyloxy derivative (V) in the usual manner by reaction with an alkylsulfonic acid chloride, preferably methanesulfonyl chloride. Displacement of the sulfonyloxy function by reaction with metal halides, sodium azide, potassium thiocyanate and the potassium salt of a lower thioalkanoic acid provides the novel compounds of this invention defined by formula (VI).

Further transformation provides other of the novel compounds of this invention. Thus, catalytic hydrogenation of the 15-azido derivative (VI, X'=N$_3$) gives the 15-amino derivative (VII), and methanolic methoxide treatment of the 15-acetylthio derivative (VI, X' =

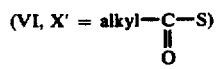

) gives the 15-mercapto derivative (VIII). Careful saponification of (VI), (VII), or (VIII) provides the carboxylic acids of this invention and reesterification provides other of the esters of this invention.

The 9-keto derivatives (IX) of this invention can be converted to the 9-hydroxy derivatives. If this conversion is effected with sodium borohydride, the product is a mixture of 9α- and 9β-hydroxy derivatives (XI + XII). When the reaction is carried out with lithium perhydro-9b-boraphenalyl hydride (X) [H. C. Brown and W. C. Dickason, Journ. Amer. Chem. Soc., 92, 709 (1970)], the product is at least predominantly the 9α-hydroxy derivative (XI), wherein the 9-hydroxy group is cis to the adjacent side-chain bearing the carboxylic acid or ester function.

(IX)

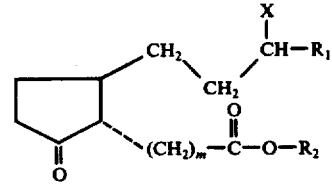

(X)

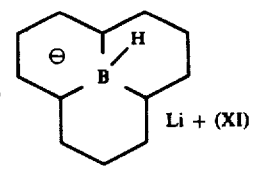

(XI)

-continued

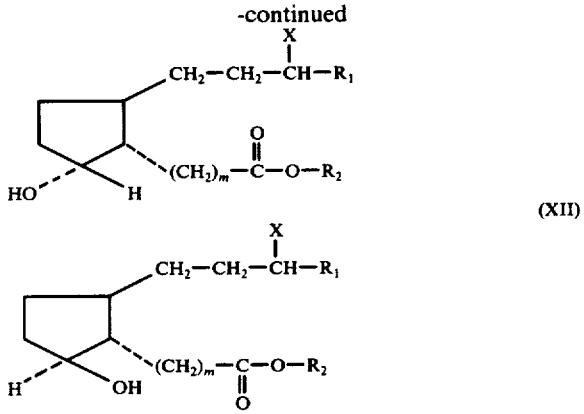

(XII)

All of the compounds of this invention can be isolated and purified by conventional methods. Isolation can be accomplished, for example, by dilution of the reaction mixture with water, extraction with a water-immiscible solvent such as methylene chloride, ethyl acetate, benzene, cyclohexane, ether, toluene and the like, chromatography, adsorption on ion-exchange resins, distillation, or a combination of these. Purification of the compounds of this invention can be accomplished by means known in the art for the purification of prostaglandins and lipids, fatty acids, and fatty esters. For example, reverse phase partition chromatography, countercurrent distribution adsorption chromatography on acid washed Florisil ® (synthetic magnesium silicate) and acid washed silica gel, preparative paper chromatography, preparative thin layer chromatography, chromatography over silver loaded cation exchange resins, and combinations thereof can be used effectively to purify the compounds produced by the processes of this invention.

All the novel compounds of this invention having assymmetric carbon atoms can be produced as racemic mixtures. These racemic mixtures can be resolved at appropriate stages by methods of resolution well known in the art. For example, acids can be treated with an optically active base such as cinchonine, quinine, brucine, d- or 1-α-phenylethylamine and the like to produce diastereoisomeric salts which can be separated by crystallization. Alternatively, the acid may be esterified with an optically active alcohol, e.g., d- or 1-menthol, estradiol 3-acetate, etc., and the diastereoisomeric esters then resolved.

Resolution of the racemic prostaglandin-like compounds of this invention can also be accomplished by reverse phase and absorption chromatography on an optically active support and adsorbent and by selective transformation of one isomer with a biologically-active prostaglandin transforming system. Such transformations can be carried out by incubation or perfusion using methods well established in the art, followed by isolation and recovery of the isomer resistant to the metabolic transformation applied. It is to be understood that the pictorial representation of the compounds of the present process is to be construed as inclusive of other forms including enantiomers and racemates, and not to be construed as limited to the particular forms shown.

It is also possible to prepare certain of the possible diastereomers by appropriate transformation from isomerically pure starting materials, in particular compounds (XIII) and (XIV), which are available from the sea coral Plexaura homomalla and which correspond to compound (IV) above.

Compound (XIII) has all its asymetric carbon atoms in the same configuration as found in the mammalian prostaglandins and is obtained by total hydrogenation of the prostaglandin $A_2$ diester (XV) followed by saponification and reesterification. Compound (XIV) which has the 15R configuration has been reported by R. E. Spraggins [Dissertation submitted to the University of Oklahoma, 1970; Dissertation Abstracts 31¹, 3934B (1971)] and is prepared in the same way as (XIII) from the 15R diastereomer corresponding to (XV).

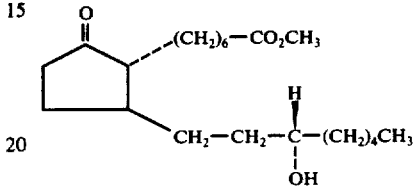

(XIII)

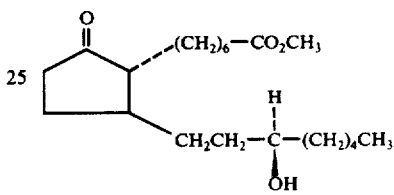

(XIV)

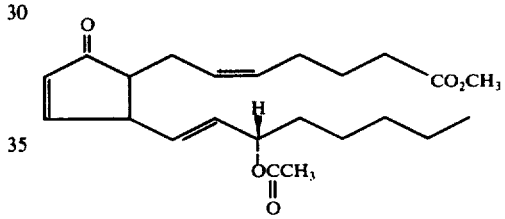

(XV)

The products of this invention have potential utility as hypotensive agents, agents for the inhibition of platelet aggregating, bronchodilators, antimicrobial agents, anti-convulsants, abortifacients, agents for the induction of labor, agents for the induction of menses, fertility-controlling agents, central nervous system regulatory agents, salt and water-retention regulatory agents, diuretics, fat metabolic regulatory agents and as serum-cholesterol lowering agents. Certain of the novel compounds of this invention possess utility as intermediates for the preparation of other of the novel compounds of this invention.

The compounds of this invention are effective inhibitors of gastric acid secretion and of ulcer development in experimental animals and thus are potentially valuable as agents for the control of gastric acid secretion, gastric erosion, and as anti-ulcer agents.

Gastric acid secretion inhibitory action is usually measured by the "Shay" techniques with some modification. [Shay, H., Sun, D. and Gruenstein, M.: "A quantitative method for measuring spontaneous gastric secretion in the rat," Gastroenterology 26: 906-913 (1954); Shay, H., Komarov, S. A., Fels, S. S., Meranze, D., Gruenstein, M. and Siplet, H.: "A simple method for the uniform production of gastric ulceration in the rat," Gastroenterology 5: 43-61 (1945)]. The Shay rat assay has been cited in a recent authoritative review as "probably the best single test for prediction of clinical usefulness" [Brodie, Gastroenterology, 58, 125-134 (1968)].

This procedure as adapted in our laboratories was carried out as follows. The rats (male, CFE strain) were starved for 48 hours (water was given ad libitum) to permit evacuation of stomach contents. On the morning of the experiment, under ether anesthesia, the abdominal region was shaved and a midline incision (1–1½ inches) was made with a scalpel. With the help of a closed curved hemostat the duodenum was picked up. Upon getting the duodenum into view, fingers were used to pull the stomach through the opening, the stomach was then gently manipulated with fingers to rid stomach of air and residual matter which were pushed through the pylorus. (This manipulation provides for enhanced and uniform acid secretion.) Two 5-inch sutures were drawn under the pyloric-duodenal puncture. A ligature, at the juncture, was formed with one of the threads. A second ligature was also formed but not tightened.

The test compounds or the vehicle (usually 1 ml./100 g. body weight) were injected into the duodenum as close as possible to the first ligature. After injection the second ligature was tightened below the injection site to minimize leakage. The stomach was placed back through the opening into the abdominal cavity, the area of incision was washed with saline and the incision was closed with autoclips.

Three hours later, the rats were decapitated and exsanguinated, taking care that blood does not drain into the esophagus. The abdominal cavity was exposed by cutting with scissors and the esophagus close to the stomach was clamped off with a hemostat, the stomach was removed by cutting above the hemostat (the esophagus was cut) and between the two sutures. Extraneous tissue was removed, the stomach washed with saline and blotted on gauze. A slit was carefully made in the stomach held over a funnel and the contents were collected in a centrifuge tube. The stomach was further cut along the outside edge and turned inside-out. Two ml. of water were used to wash the stomach contents into the respective centrifuge tube. The combined stomach contents and wash were then centrifuged out for 10 minutes in the International Size 2 Centrifuge (setting at 30). The supernatant was collected, volume measured and recorded, 2 drops of a phenolphthalein indicator 1% in 95% ethanol) were added and the solution was titrated with 0.02N NaOH (or with 0.04N NaOH when large volumes of stomach contents were encountered) to pH 8.4 (because of usual coloring of the stomach contents, phenolphthalein was merely used to permit visual indication that the end point was near) and the amount of acid present was calculated. Compounds inducing inhibition of gastric acid secretion of 20% or more are considered active. Representative results obtained with this assay are given in the following Table.

TABLE I

Inhibition of Gastric Acid Secretion in the Pylorus - ligated Rat ("Shay-Rat")

| Compound | Intraduodenal Dose, mg./kg. | % Inhibition |
|---|---|---|
| Ethyl 9-oxo-15-azidoprostanoate | 100 | 52 |
| 9-Oxo-15-azidoprostanoic Acid | 100 | 30 |
| Ethyl 9-oxo-15-mercaptoprostanoate | 200 | 32 |
| Ethyl 9-oxo-15-chloroprostanoate | 100 | 24 |
| Ethyl 9-oxo-15-thiocyanoprostanoate | 100 | 57 |

This invention will be described in greater detail in conjunction with the following specific examples.

EXAMPLE 1

Preparation of 2-carbalkoxy(methyl/ethyl)-2-(4-carbethoxybutyl)-cyclopentan-1-one To a stirred solution of the sodium cyclopentanone carboxylate enolate in dimethoxyethane, prepared from 187 g. (1.248 moles) of 2-cyclopentanone carboxylate (mixed methyl and ethyl esters), 52.4 g. (1.248 moles) sodium hydride (57.2% in mineral oil) and 1.61 l. of dimethoxyethane, is added dropwise 309 g. (1.212 moles) of ethyl 5-iodovalerate. The reaction mixture is stirred and heated at reflux for 18 hours. The mixture is cooled and filtered. The solvent is removed from the filtrate by evaporation and the residue is poured into dilute hydrochloric acid and extracted with ether. The combined extracts are washed with water and saline, dried over magnesium sulfate and evaporated to give an oil. The oil is distilled under reduced pressure to give 274 g. of a light yellow oil, b.p. 140°–143° C. (0.17 mm).

EXAMPLE 2

Preparation of 2-(4-carboxybutyl)cyclopentan-1-one

A stirred mixture of 274 g. of 2-carbalkoxy(mixed methyl and ethyl esters)-2-(4-carbethoxybutyl)cyclopentan-1-one (Example 1), 600 ml. of 20% hydrochloric acid and 325 ml. of acetic acid is heated at reflux for 20 hours. Solution occurs in approximately ½ hour. The solution is cooled and diluted with water and extracted with ether. The combined extracts are washed with saline and dried over magnesium sulfate and evaporated. The residue is evaporated twice with toluene to give 144 g. of an oil.

EXAMPLE 3

Preparation of 2-(4-carbethoxybutyl)cyclopentan-1-one

A stirred solution of 124 g. (0.673 mole) of 2-(4-carboxybutyl)cyclopentan-1-one (Example 2), 800 ml. of ethanol and 1 g. of p-toluenesulfonic acid monohydrate is heated at reflux for 18 hours. The solvent is evaporated and the residue is dissolved in ether. The ether solution is washed with saline, dilute sodium bicarbonate solution and again with saline, dried over magnesium sulfate and evaporated. The oil is distilled under reduced pressure to give 149 g. of a colorless oil, b.p. 106°–109° C. (0.23 mm).

EXAMPLE 4

Preparation of 2-carbalkoxy(methyl/ethyl)-2-(3-carbethoxypropyl)-cyclopentan-1-one In the manner described in Example 1, treatment of 2-cyclopentanone carboxylate (mixed methyl and ethyl esters) with sodium hydride in dimethoxyethane followed by ethyl 4-iodobutyrate gives a yellow oil, b.p. 136°–137° C. (0.16 mm).

EXAMPLE 5

Preparation of 2-(3-carboxypropyl)cyclopentan-1-one

In the manner described in Example 2, treatment of 2-carbalkoxy(mixed methyl and ethyl esters)-2-(3-carbethoxypropyl)cyclopentan-1-one (Example 4) with a 20% hydrochloric acid and acetic acid mixture gives a yellow oil.

EXAMPLE 6

Preparation of 2-(3-carbethoxypropyl)cyclopentan-1-one

In the manner described in Example 3, treatment of 2-(3-carboxypropyl)cyclopentan-1-one (Example 5) with p-toluene-sulfonic acid monohydrate in ethanol gives a colorless oil, b.p. 93° C. (0.10 mm).

EXAMPLE 7

Preparation of ethyl and methyl 2-(6-carbethoxyhexyl)-1-cyclopentanon-2-carboxylate In the manner described in Example 1, ethyl and methyl 2-cyclopentanone carboxylate is reacted with ethyl 7-bromoheptanoate to furnish the subject product, b.p. 147° C. (0.09 mm).

EXAMPLE 8

Preparation of 2-(6-carboxyhexyl)cyclopentan-1-one

In the manner described in Example 2, ethyl and methyl 2-(6-carbethoxyhexyl)-1-cyclopentanone-2-carboxylate (Example 7) is hydrolyzed to furnish the subject product, b.p. 143° C. (0.05 mm).

EXAMPLE 9

Preparation of 2-(6-carbethoxyhexyl)cyclopentan-1-one

In the manner described in Example 3, 2-(6-carboxyhexyl)cyclopentan-1-one (Example 8) is esterified to furnish the subject product, b.p. 110° C. (0.03 mm).

EXAMPLE 10

Preparation of 1-acetoxy-2-(6-carbethoxyhexyl)cyclopent-1ene

A stirred solution of 100 g. of 2-(6-carbethoxyhexyl)-cyclopentan-1-one (Example 9) in 250 ml. of acetic anhydride containing 0.940 g. of p-toluenesulfonic acid monohydrate is heated to boiling under partial reflux allowing distillate at 118° C. or less (i.e., acetic acid) to escape through a Vigreaux column equipped with a condenser to collect the distillate. After 16 hours, during which period acetic anhydride is added in portions in order to keep the solvent level at at least 100 ml., the solution is cooled and poured cautiously into a stirred cold mixture of saturated sodium bicarbonate solution (400 ml.) and hexane (250 ml.). The resulting mixture is stirred for an additional 30 minutes during which period solid sodium bicarbonate is added periodically to insure a basic solution. The hexane layer is separated and washed with saturated sodium chloride solution, dried with anhydrous magnesium sulfate and taken to dryness. Distillation of the residual oil gives 102 g. (87%) of pale yellow oil, b.p. 118° C. (0.07 mm).

EXAMPLE 11

Preparation of 1-acetoxy-2-(3-carbethoxypropyl)cyclopent-1-ene

In the manner described in Example 10, treatment of 2-(3-carbethoxypropyl)cyclopentan-1-one (Example 6) with acetic anhydride and p-toluenesulfonic acid mohohydrate gives a yellow oil, b.p. 98°–103° C. (0.35 mm).

EXAMPLE 12

Preparation of 1-acetoxy-2-(4-carbethoxybutyl)cyclopent-1-ene

In the manner described in Example 10, treatment of 2-(4-carbethoxybutyl)cyclopentan-1-one (Example 3) with acetic anhydride and p-toluenesulfonic acid monohydrate gives a yellow oil, b.p. 109°–110° C. (0.37 mm).

EXAMPLE 13

Preparation of 2-(6-carbethoxyhexyl)cyclopent-2-en-1-one

To a rapidly stirred mixture of 50 g. of 1-acetoxy-2-(6-carbethoxyhexyl)cyclopent-1-ene (Example 10) in 150 ml. of chloroform, 200 ml. of water and 18.8 g. of calcium carbonate, cooled in an ice bath, is added dropwise over a period of about 30 minutes, a solution of 30 g. of bromine in 50 ml. of carbon tetrachloride. After stirring for an additional 45 minutes the chloroform layer is separated and washed successively with dilute sodium thiosulfate solution, saturated sodium chloride solution, dried with anhydrous magnesium sulfate and taken to dryness under reduced pressure.

The residual oil is dissolved in 50 ml. of N,N-dimethylformamide and added to a mixture of 33 g. of lithium bromide and 32 g. of lithium carbonate in 375 ml. of N,N-dimethylformamide, previously dried by refluxing with 375 ml. of benzene under a Dean-Stark apparatus followed by distillation of the benzene. The mixture is stirred at the reflux temperature for 30 minutes, then cooled and poured into 850 ml. of ice-cold water. The resulting mixture is acidified (cautiously) with 4N hydrochloric acid and extracted with ether three times. The combined ether extracts are washed with saturated sodium chloride solution, dried with anhydrous magnesium sulfate and taken to dryness under reduced pressure to afford 41.5 g. of an amber oil. In order to convert any isomeric material to the desired product, 41.5 g. of the above material is treated with 0.500 g. of p-toluenesulfonic acid monohydrate in 450 ml. of absolute alcohol at the reflux temperature for 18 hours. The solution is taken to dryness under reduced pressure. The resulting gum is dissolved in ether and washed with saturated sodium bicarbonate solution, saturated sodium chloride solution, dried with anhydrous magnesium sulfate and taken to dryness under reduced pressure. The residual oil is distilled to give 30.2 g. of product; b.p. 118° C. (0.05 mm); $\lambda_{max}^{MeOH}$ 229 m$\mu$ (E9950): $\lambda_{max}$ 5.75, 5.85, 6.15, 8.45 $\mu$; vapor phase chromatography shows 99% product, containing 1% 2-(6-carbethoxyhexyl)cyclopentan-1-one.

This product can be purified by the following procedure. A mixture of 120 g. of 2-(6-carbethoxyhexyl)-2-cyclopentenone, containing approximately 5% of the saturated analogue, and 7.67 g. (10 mole percent) of p-carboxyphenylhydrazine in 400 ml. of absolute ethanol is stirred at ambient temperatures for 18 hours and is then refluxed for 1 hour. The mixture is cooled, the solvent is evaporated, and the residue is taken up into 150 ml. of chloroform and passed through a column of 450 g. of aluminum oxide (Merck). The filtrate is evaporated to yield a colorless oil containing < 0.5% of the saturated impurity.

EXAMPLE 14

Preparation of 2-(3-carbethoxypropyl)cyclopent-2-en-1-one

In the manner described in Example 13, bromination of 1-acetoxy-2-(3-carbethoxypropyl)cyclopent-1-ene (Example 11) followed by dehydrobromination with lithium bromide and lithium carbonate is productive of the subject compound.

EXAMPLE 15

Preparation of 2-(4-carbethoxybutyl)cyclopent-2-en-1-one

In the manner described in Example 13, treatment of 1-acetoxy-2-(4-carbethoxybutyl)cyclopent-1-ene (Example 12) with bromine and subsequent treatment of the brominated product with a mixture of lithium bromide and lithium carbonate in N,N-dimethylformamide is productive of the subject compound. Treatment of this product with p-carboxyphenylhydrazine by the procedure of Example 13 furnishes a product which contains less than 0.5% of the corresponding saturated ketone.

EXAMPLE 16

Preparation of 1-methoximino-2-(6-carbethoxyhexyl)-2-cyclopentene

To a mixture of 35.97 g. (0.151 mole) of 2-(6-carbethoxyhexyl)-2-cyclopentenone (Example 13) and 15.0 g. (0.180 mole) of methoxyamine hydrochloride in 300 ml. of absolute ethanol is added 25 ml. of pyridine and the resulting solution is stirred for 20 hours at ambient temperatures. The solvent is evaporated and the residue is partitioned between water and diethyl ether. The organic phase is washed with water and saturated brine, dried ($Na_2SO_4$), and the solvent is evaporated to yield an oil. Distillation yields 38.7 g. of a colorless oil, b.p. 115°–118° C. (0.075 mm). IR (film): 1740, 1627, 1053, 890 cm$^{-1}$. $\lambda_{max}$ (MeOH) 243 (13,000). NMR$\delta$(CDCl$_3$): 3.89.

EXAMPLE 17

Preparation of 1-methoximino-2-(7-hydroxyheptyl)-2-cyclopentene

To an ice cooled solution of 34.10 g. (0.128 mole) of 1-methoximino-2-(6-carbethoxyhexyl)-2-cyclopentene (Example 16) in 200 ml. of benzene under nitrogen is added dropwise 225 ml. of a 25% solution of diisobutyl aluminum hydride in hexane. The resulting solution is stirred for 2 hours at 0°–5° C., poured onto ice and dilute hydrochloric acid, and the aqueous phase is saturated with sodium chloride. The organic phase is separated, washed with saturated brine, dried ($Na_2SO_4$), and evaporated to yield an oil. The latter is dissolved in 100 ml. of hot hexane and cooled to yield 24.3 g. of crystals, m.p. 62°–64° C. IR (KBr) 3260, 1630, 1059, 893 cm$^{-1}$. $\lambda_{max}$ 243 (14,200). NMR (CDCl$_3$)$\delta$: 2.37.

EXAMPLE 18

Preparation of 1-methoximino-2-(7-p-toluenesulfonyloxyheptyl)-2-cyclopentene

To a solution o 5.00 g. (0.0222 mole) of 1-methoximino-2-(7-hydroxyheptyl)-2-cyclopentene (Example 17) in 50 ml. of dry pyridine at 0° C. is added 8.45 g. (0.0444 mole) of p-toluenesulfonyl chloride and the resulting solution is chilled at 5° C. overnight. The mixture is partitioned between 300 ml. of ice water and diethyl ether. The organic phase is washed with 1:1 ice cold hydrochloric acid, cold water, and cold saturated brine, dried ($NaSO_4/K_2CO_3$), and evaporated under reduced pressure at room temperature to yield an oil. The latter is dissolved in 600 ml. of hexane, treated with 0.5 g. of Darco, filtered and evaporated to yield 7.7 g. of a colorless oil. IR (film) 1600, 1192, 1182, 1053, 890 cm$^{-1}$. $\lambda_{max}$ (MeOH) 228 and 243.

EXAMPLE 19

Preparation of 1-methoximino-2-(8,8-dicarbethoxyoctyl)-2-cyclopentene

To an alcoholic solution of sodiodiethyl malonate, prepared from 0.847 g. (0.0368 g. atoms) of sodium, 100 ml. of absolute ethanol, and 7.05 g. (0.0440 mole) of diethyl malonate is added 7.7 g. of the tosylate of Example 18 and the mixture is refluxed for 2 hours under a nitrogen atmosphere. The mixture is partitioned between cold dilute hydrochloric acid and diethyl ether, and the organic phase is washed with water and saturated brine, dried ($Na_2SO_4$), and evaporated to yield an oil. The excess diethyl malonate is distilled off under reduced pressure to yield 6.45 g. of a yellowish oil. IR (film) 1755, 1728, 1625, 1054, 890 cm$^{-1}$.

EXAMPLE 20

Preparation of 1-methoximino-2-(8,8-dicarboxyoctyl)-2-cyclopentene

A mixture of 6.45 g. of the diester of Example 19 and 6.72 g. of potassium hydroxide in 150 ml. of 1:1 aqueous methanol is refluxed for 1 hour, cooled, and is partitioned between water and diethyl ether. The aqueous phase is acidified with hydrochloric acid, extracted with ether, and the organic phase is washed with water and saturated brine, dried ($Na_2SO_4$) and evaporated to yield a solid. The solid is crystallized from benzene to yield 4.15 g. of tan crystals, m.p. 135°–137° C. (—$CO_2$).

EXAMPLE 21

Preparation of 1-methoximino-2-(8-carboxyoctyl)-2-cyclopentene

A solution of 3.926 g. (0.0126 mole) of the diacid of Example 20 in 20 ml. of xylene is refluxed for 1.5 hours, cooled, and evaporated to yield a tan solid. IR (KBr) 1720, 1618, 1179, 1050, 986 cm$^{-1}$.

EXAMPLE 22

Preparation of 2-(8-carboxyoctyl)cycopent-2-en-1-one

The acid methoxime from Example 21 is refluxed for 5 hours with 55 ml. of acetone and 20 ml. of 2N hydrochloric acid. The mixture is cooled, the solvent is evaporated, and the residue is partitioned between water and diethyl ether. The organic phase is washed with water and saturated brine, dried ($Na_2SO_4$), and evaporated to yield a tan solid. IR (KBr) 1745, 1665 cm$^{-1}$. $\lambda_{max}$ (MeOH) 228 (12,600).

EXAMPLE 23

Preparation of 2-(8-carbethoxyoctyl)cyclopent-2-en-1-one

The acid ketone from Example 22 is Fisher esterified with 100 ml. of absolute ethanol, 100 ml. of benzene, and 20 mg. of p-toluenesulfonic acid for 6 hours, cooled, and the solvent is evaporated. The resulting oil is dis-

EXAMPLE 24

Preparation of
1-methoximino-2-(5-cyanopentyl)-2-cyclopentene

A mixture of 2.75 g. (0.01 mole of 1-methoximino-2-(5-methanesulfonyloxypentyl)-2-cyclopentene (Example 23) and 1.47 g. (0.03 mole) of sodium cyanide in 20 ml. of dry N,N-dimethylformamide is heated at 65°–70° C. for 3 hours. The cooled reaction mixture is poured into water and extracted with diethyl ether. The organic phase is washed with water and saturated saline solution, dried (MgSO$_4$), and evaporated to give 1.89 g. of a light yellow oil.

EXAMPLE 25

Preparation of
1-methoximino-2-(5-carboxypentyl)-2-cyclopentene

A mixture of 1.89 g. (0.0092 mole) of 1-methoximino-2-(5-cyanopentyl)-2-cyclopentene (Example 24) and 1 g. (0.025 mole) of sodium hydroxide in 50 ml. of 1:1 aqueous-ethanol is refluxed for 48 hours, cooled, and partitioned between water and diethyl ether. The aqueous phase is acidified with hydrochloric acid, extracted with diethyl ether, and the organic phase is washed with water and saturated saline solution, dried (MgSO$_4$), and evaporated to give 1.86 g. of a yellow oil.

EXAMPLE 26

Preparation of 2-(5-carboxypentyl)-2-cyclopentenone

A solution of 1.86 g. (0.00825 mole) 1-methoximino-2-(5-carboxypentyl)-2-cyclopentene (Example 25) in 44 ml. of acetone and 13.1 ml. of 2N hydrochloric acid is refluxed for 5 hours. The solvent is partially evaporated and a solid precipitates and is collected. The residue is extracted with diethyl ether and the organic phase is washed with saturated saline solution, dried (MgSO$_4$), and evaporated to yield additional solid. The combined solid material is crystallized from ether/pet ether (30°–60° C°) to yield crystalline material, m.p. 70°–72° C.

EXAMPLE 27

Preparation of
2-(5-carbethoxypentyl)-2-cyclopentenone

A solution of 1.309 g. (0.00668 mole) of 2-(5-carboxypentyl)-2-cyclopentenone (Example 26) and 90 ml. of p-toluenesulfonic acid in 150 ml. of ethanol is refluxed for 18 hours. The solvent is evaporated and the residue is dissolved in ether. The organic phase is washed with water, sodium bicarbonate solution, and saturated saline solution, dried (MgSO$_4$), and evaporated to give 1.371 g. of a light yellow oil.

EXAMPLE 28

Preparation of
2-(5-acetoxypentyl)-2-carbomethoxy/carbethoxycyclopentanone

A mixture of sodiocyclopentanone carboxylate, prepared from 1200 g. (8.0 moles) of cyclopentanone carboxylate (methyl and ethyl esters) and 200 g. (8.3 moles) of mineral oil free sodium hydride in 10 l. of 1,2 -dimethoxyethane, 1320 g. (8.0 moles) of 5-chloro-1-amyl acetate [M. E. Synerholm, Journ. Amer. Chem. Soc., 69, 2681 (1947)], and 1200 g. (8.0 moles) of sodium iodide is refluxed under nitrogen for 18 hours. The mixture is cooled, concentrated to 4 l. and partitioned between dilute hydrochloric acid and diethyl ether. The organic phase is washed with water and saturated brine, dried (MgSO$_4$), and evaporated to yield 1920 g. of an oil.

EXAMPLE 29

Preparation of
2-(5-hydroxypentyl)cyclopentanone/2-(5-acetoxypentyl)-cyclopentanone A mixture of 4,500 g. (16.2 moles) of 2-(5-acetoxypentyl)-2-carbomethoxy/carboethoxy-cyclopentanone (Example 28), 2.2 l. of glacial acetic acid, 1 l. of concentrated hydrochloric acid, and 1.1 of water is refluxed for 18 hours, cooled, and partitioned between saturated brine and benzene. The organic phase is washed with saturated brine, dried (MgSO$_4$), and evaporated in vacuo to yield 3155 g. of an oil.

EXAMPLE 30

Preparation of
1-acetoxy-2-(5-acetoxypentyl)-1-cyclopentene

A solution of 400 g. (2.04 moles) of a mixture of 2-(5-hydroxypentyl)cyclopentanone and 2-(5-acetoxypentyl)cyclopentanone (Example 29) and 4.0 g. of p-toluenesulfonic acid monohydrate in 1 l. of acetic anhydride is refluxed at a rate to maintain a steady distillation of acetic acid from the reaction through a helix-packed fractionation column. The reaction is continued with the addition of acetic anhydride to maintain a constant volume until complete conversion of starting materials to product is evident. The mixture is cooled and partitioned between 2 l. of hexane and 3 l. of cold water containing solid sodium bicarbonate to maintain a neutral pH. The organic phase is washed with saturated brine, dried (MgSO$_4$), and evaporated to yield 452 g. of an oil.

EXAMPLE 31

Preparation of 2-(5-acetoxypentyl)-2-cyclopentenone

To a well stirred mixture of 405 g. (4.05 moles of calcium carbonate, 3 l. of water, and 2.5 l. of chloroform cooled to 5° C is added simultaneously 1016 g. (4.0 moles) of 1-acetoxy-2-(5-acetoxy-pentyl)-1-cyclopentene (Example 30) and a solution of 648 g. (4.05 moles) of bromine in 500 ml. of carbon tetrachloride at a rate to maintain a temperature below 10° C. The mixture is stirred for half an hour after addition of the reagents and the phases are then separated. The organic phase is washed with 2% sodium thiosulfate solution, water, and saturated brine, dried (MgSO$_4$), and evaporated in vacuo to an oil. The oil is immediately added to a refluxing slurry of 500 g. (5.0 moles) of calcium carbonate in 2.5 l of N,N-dimethylacetamide under nitrogen and the mixture is then refluxed for thirty minutes. The mixture is cooled, filtered, and partitioned between water and diethyl ether. The organic phase is washed with water and saturated brine, dried (MgSO$_4$), and evaporated to yield 757 g. of an oil, b.p. 116°–118° C. (0.25 mm.).

EXAMPLE 32

Preparation of 1-methoximino-2-(5-acetoxypentyl)-2-cyclopentene

In the manner described for Example 16, 2-(5-acetoxypentyl)-2-cyclopentenone (Example 31) is treated with methoxyamine hydrochloride in pyridine and ethanol to yield the subject compound, b.p. 101°-103° C. (0.20 mm.).

EXAMPLE 33

Preparation of 1-methoximino-2-(5-hydroxypentyl)-2-cyclopentene

A mixture of 74 g. (0.22 mole) of 1-methoximino-2-(5-acetoxypentyl)-2-cyclopentene (Example 32) and 56 g. (1.0 mole) of potassium hydroxide in 300 ml. of 1:1 aqueous methanol is refluxed for 2 hours and then cooled. The solvent is partially removed in vacuo and the residue is partitioned between saturated brine and diethyl ether. The organic phase is washed with saturated brine, dried ($MgSO_4$), and evaporated to yield an oil which crystallized, m.p. 35°-36° C.

EXAMPLE 34

Preparation of 1-methoximino-2-(5-methanesulfonyloxypentyl)-2-cyclopentene

To a cold solution of 9.85 g. (0.05 mole) of 1-methoximino-2-(5-hydroxypentyl)-2-cyclopentene (Example 33) and 7.6 g. (0.075 mole) of triethylamine in 100 ml. of methylene chloride at −10° C. is added 6.3 g. (0.055 mole) of methanesulfonyl chloride at a rate to maintain a temperature of −10° to 0° C. The mixture is then stirred for 15 minutes and then poured into ice water. The organic phase is washed with cold 10% hydrochloric acid, cold saturated sodium bicarbonate solution, and cold saturated brine, dried ($MgSO_4$), and evaporated to yield a solid, m.p. 78°-80° C.

EXAMPLE 35

Preparation of 1-methoximino-2-(6,6-dicarbethoxyhexyl)-2-cyclopentene

To a suspension of sodiodiethylmalonate in 1,2-dimethoxyethane, prepared from 248 g. (1.55 moles) of diethyl malonate and 17.2 g. (0.95 mole) of mineral oil free sodium hydride in 1 l. of 1,2-dimethoxyethane under nitrogen, is added 170 g. (0.62 mole) of 1-methoximino-2-(5-methanesulfonyloxypentyl)-2-cyclopentene (Example 34) in 1.5 l. of 1,2-dimethoxyethane and the mixture is refluxed for 5 hours. The mixture is cooled, filtered, and the solvent is evaporated. The residue is partitioned between cold dilute hydrochloric acid and water, and the organic phase is washed with saturated brine, dried ($MgSO_4$), and evaporated to remove solvent and excess diethyl malonate to yield 209 g. of an oil.

EXAMPLE 36

Preparation of 1-methoximino-2-(6,6-dicarboxyhexyl)-2-cyclopentene

In the manner described in Example 20, 1-methoximino-2-(6,6-dicarbethoxyhexyl)-2-cyclopentene is treated with potassium hydroxide in 1:1 aqueous methanol and then hydrochloric acid to yield the desired compound as crystals from diethyl ether, m.p. 110°-115° C.

EXAMPLE 37

Preparation of 1-methoximino-2-(6-carboxyhexyl)-2-cyclopentene

A solution of 141 g. (0.50 mole) of 1-methoximino-2-(6,6-dicarboxyhexyl)-2-cyclopentene in 500 ml. of bis-(2-methoxyethyl) ether is refluxed for 2 hours, cooled, and evaporated to yield an oil. The latter is crystallized from hexane to yield 92 g. of solid, m.p. 70°-72° C.

EXAMPLE 38

Preparation of 2-(6-carboxyhexyl)-2-cyclopentenone

In the manner described in Example 22, treatment of 1-methoximino-2-(6-carboxyhexyl)-2-cyclopentene (Example 37) with acetone and 2N hydrochloric acid at reflux provides the subject compound.

EXAMPLE 39

Preparation of 2-(6-carbethoxyhexyl)-2-cyclopentenone

Fischer estification of 2-(6-carboxyhexyl)-2-cyclopentenone (Example 38) in the manner of Example 23 provides the subject compound.

EXAMPLE 40

Preparation of 2-(7-cyanoheptyl)-1-methoximino-2-cyclopentene

Treatment of 1-methoximino-2-(7-p-toluenesulfonyloxy)-2-cyclopentene (Example 18) with sodium cyanide in the manner of Example 24 is productive of the subject compound.

EXAMPLE 41

Preparation of 2-(7-carboxyheptyl)-1-methoximino-2-cyclopentene

Alkaline hydrolysis of 2-(7-cyanoheptyl)-1-methoximino-2-cyclopentene (Example 40) by the procedure of Example 25 is productive of the subject compound.

EXAMPLE 42

Preparation of 2-(7-carboxyheptyl)-2-cyclopenten-1-one

Hydrolysis of the methoxime of Example 41 with acetone-hydrochloric acid by the procedure of Example 26 is productive of the subject compound.

EXAMPLE 43

Preparation of 2-(7-carbethoxyheptyl)-2-cyclopenten-1-one

Fischer estification of the carboxylic acid of Example 42 by the procedure of Example 27 is productive of the subject compound.

EXAMPLE 44

Preparation of 2-(6-carbo-n-butoxyhexyl)cyclopent-2-en-1-one

A solution of 50 g. of 2-(6-carboxyhexyl)cyclopent-2-en-1-one [Bagli et al., *Tetrahedron Letters*, No. 5, 465 (1966)] in 1400 ml. of n-butanol containing 2.7 g. of p-toluenesulfonic acid monohydrate is allowed to stand at room temperature in a stoppered flask for about 24 hours. The solution is taken to dryness. The residue is taken up in ether and the ethereal solution is washed several times with saline solution, dried with anhydrous magnesium sulfate, and taken to dryness to afford the subject butyl ester.

EXAMPLES 45-47

Treatment of 2-(6-carboxyhexyl)cyclopent-2-en-1-one by the procedure of Example 44 with the appropriate alcohol affords the esters of the following table.

TABLE I

| Ex. | Alcohol | Product Ester |
| --- | --- | --- |
| 45 | isopropanol | 2-(6-carboisopropoxyhexyl)cyclopent-2-en-1-one |
| 46 | methanol | 2-(6-carbomethoxyhexyl)cyclopent-2-en-1-one |
| 47 | 1-hydroxy-n-decane | 2-(6-carbo-n-decyloxyhexyl)cyclopent-2-en-1-one |

EXAMPLE 48

Preparation of 3-(tert-butoxy)-1-iodooctane

Into a solution of 16.7 g. of 1-iodo-3-octanol [Shriner et al., J. Org. Chem. 4, 103 (1939)] in 250 ml. of methylene chloride is bubbled isobutylene at a fast rate until the solution is saturated. The solution is cooled and 2 ml. of concentrated sulfuric acid is added. The solution is stoppered and allowed to stand at room temperature for 3 days. After the solution is poured into 300 ml. of 5% sodium carbonate, the organic phase is separated, washed with brine, dried with anhydrous magnesium sulfate and evaporated to dryness. Distillation gave 13.9 g. (68%) of product, b.p. 59° C. (0.008 mm).

EXAMPLE 49

Preparation of 15-(tert-butoxy)-9-oxoprostanoic acid, ethyl ester

To a Grignard solution, prepared from 5.05 g. of magnesium and 65.8 g. of 3-(tert-butoxy)-1-iodooctane in 150 ml. of diethyl ether under nitrogen atmosphere, is added 4.0 g. of copper iodide-tri-n-butylphosphine complex followed by dropwise addition of 49 g. of 2-(6-carbethoxyhexyl)cyclopent-2-en-1-one [Hardegger et al., Helv. Chim. Acta 50, 2501 (1967)] and the resulting mixture is stirred for 18 hours. Saturated ammonium chloride (110 ml.) is added followed by 100 ml. of water and 100 ml. of diethyl ether. Unreacted magnesium is removed by filtration. The ethereal layer is washed successively with aqueous sodium thiosulfate solution, ammonium chloride solution, and water, dried over magnesium sulfate and taken to dryness to give an oil. Distillation at 0.05 mm. (bath 100°-185° C.) gives 45.4 g. of material containing unreacted starting material and 30 g. (85% yield based on non-recovered starting material; see below) of residue which contains the desired product. This material is chromatographed on silica gel. The product is eluted with diethyl ether to give 25.2 g. (71% based on recovered starting material) of a syrup; this material has no significant ultraviolet absorption; $\lambda_{max}^{KBr}$ 5.74, 7.20, 7.35, 8.35 $\mu$; nmr 2H quartet $\delta$4.09 (OCH$_2$ of ester), 1H broad singlet 3.57 (carbinolic proton), 5H overlapping multiplets 2.0–2.4 (protons next to C=O), 3H triplet 1.22 (CH$_3$ of ethyl), 9H singlet 1.17 (CH$_3$'s to t-butyl) and 3H triplet 0.9 (terminal methyl); mass spectrum: m/e 424.

EXAMPLE 50

Preparation of 15-hydroxy-9-oxoprostanoic acid, ethyl ester

A solution of 25 g. of 15-(tert-butoxy)-9-oxoprostanoic acid, ethyl ester in 100 ml. of trifluoroacetic acid is stirred in an ice bath for 1 hour and is then poured into 500 ml. of ice water and extracted several times with chloroform. The combined chloroform extracts are washed with saturated sodium bicarbonate solution, saturated sodium chloride solution, dried with anhydrous magnesium sulfate, and taken to dryness. The resulting oil is dissolved in 200 ml. of 1N ammonium hydroxide in ethanol, kept at ambient temperature for 15 minutes, then taken to dryness. The residual oil is dissolved in chloroform and washed with 1N hydrochloric acid, saturated sodium chloride solution, dried and taken to dryness to give 21.7 g. (100%) of product as a yellow syrup. There is essentially no uv absorption; $\lambda_{max}^{KBr}$ 2.90, 5.75, 8.45 $\mu$; nmr 2H quartet $\delta$4.13 (OCH$_2$ of ester), 1H broad singlet 3.63 (carbinolic proton), 3H triplet (CH$_3$ of ester) and 3H distorted triplet 0.92 (terminal methyl); mass spectrum: m/e 368.

EXAMPLE 51

Preparation of 3-(tert-butoxy)-1-iodohexane

A mixture of 23.4 g. of 1-chloro-3-hexanol [Fourneau, et. al., Bull. Soc. Chem. France. 25, 367 (1919)] in 300 ml. of 2-butanone containing 30 g. of sodium iodide is stirred at the reflux temperature for 18 hours. The cooled solution is filtered and the mother liquor is taken to dryness. Distillation of the residue affords 32.9 g. (84%) of 1-iodo-3-hexanol, b.p. 105° C. (10 mm). Treatment of this material in 500 ml. of methylene chloride, containing 4 ml. of concentrated sulfuric acid, with isobutylene according to the procedure described in Example 48 gives 27 g. of crude material. Chromatography on florisil affords 16 g. of product; $\lambda$max. 7.22 and 7.37 $\mu$ (tert-butyl group).

EXAMPLE 52-70

Treatment of the various cyclopentenone esters listed in Table II below with the 3-t-butoxyalkyl magnesium iodide, also listed in the table, in the presence of tributylphosphine cuprous iodide complex all in the manner described in Example 49 above is productive of the 15-(tert-butoxy)-9-oxo-prostanoates of the table.

TABLE 2

| Ex. | Starting cyclopentenone of Example | Grignard Reagent | Product 15-(tert-butoxy)-9-oxo-prostanoates |
| --- | --- | --- | --- |
| 52 | 13 | 3-t-butoxyhexyl magnesium iodide | Ethyl 9-oxo-15-t-butoxy-19,20-dinor-prostanoate |
| 53 | 14 | " | Ethyl 9-oxo-15-t-butoxy-5,6,7,19,20-pentanor-prostanoate |
| 54 | 15 | " | Ethyl 9-oxo-15-t-butoxy-6,7,19,20-tetranor-prostanoate |
| 55 | 23 | " | Ethyl 9-oxo-15-t-butoxy-7a,7b-bishomo-19,20-dinor-prostanoate |
| 56 | 27 | " | Ethyl 9-oxo-15-t-butoxy-7,19,20-trinor-prostanoate |
| 57 | 43 | " | Ethyl 9-oxo-15-t-butoxy-7a-homo-19,20- |

TABLE 2-continued

| Ex. | Starting cyclopentenone of Example | Grignard Reagent | Product 15-(tert-butoxy)-9-oxo-prostanoates |
|---|---|---|---|
| 58 | 44 | " | Butyl 9-oxo-15-t-butoxy-19,20-dinor-prostanoate |
| 59 | 45 | " | Isopropyl 9-oxo-15-t-butoxy-19,20-dinor-prostanoate |
| 60 | 46 | " | Methyl 9-oxo-15-t-butoxy-19,20-dinor-prostanoate |
| 61 | 47 | " | Decyl 9-oxo-15-t-butoxy-19,20-dinor-prostanoate |
| 62 | 14 | 3-t-butoxyoctyl magnesium iodide | Ethyl 9-oxo-15-t-butoxy-5,6,7-trinor-prostanoate |
| 63 | 15 | " | Ethyl 9-oxo-15-t-butoxy-6,7-dinor-prostanoate |
| 64 | 23 | " | Ethyl 9-oxo-15-t-butoxy-7a,7b-bishomo-prostanoate |
| 65 | 27 | " | Ethyl 9-oxo-15-t-butoxy-7-nor-prostanoate |
| 66 | 43 | " | Ethyl 9-oxo-15-t-butoxy-7a-homo-prostanoate |
| 67 | 44 | " | Butyl 9-oxo-15-t-butoxy-prostanoate |
| 68 | 45 | " | Isopropyl 9-oxo-15-t-butoxy-prostanoate |
| 69 | 46 | " | Methyl 9-oxo-15-t-butoxy-prostanoate |
| 70 | 47 | " | Decyl 9-oxo-15-t-butoxy-prostanoate |

EXAMPLES 71-89

Treatment of the various 15-tert-butoxyprostanoates of Table 3 below with trifluoroacetic acid in the manner of Example 50 above is productive of the corresponding 15-hydroxyprostanoates of the table.

TABLE 3

| Ex. | Starting 15-tert-butoxyprostanoates of example | Product 15-hydroxy-9-oxo-prostanoates |
|---|---|---|
| 71 | 52 | Ethyl 9-oxo-15-hydroxy-19,20-dinor-prostanoate |
| 72 | 53 | Ethyl 9-oxo-15-hydroxy-5,6,7,19,20-pentanor-prostanoate |
| 73 | 54 | Ethyl 9-oxo-15-hydroxy-6,7,19,20-tetranor-prostanoate |
| 74 | 55 | Ethyl 9-oxo-15-hydroxy-7a,7b-bishomo-19,20-dinor-prostanoate |
| 75 | 56 | Ethyl 9-oxo-15-hydroxy-7,19,20-trinor-prostanoate |
| 76 | 57 | Ethyl 9-oxo-15-hydroxy-7a-homo-19,20-dinor-prostanoate |
| 77 | 58 | Butyl 9-oxo-15-hydroxy-19,20-dinor-prostanoate |
| 78 | 59 | Isopropyl 9-oxo-15-hydroxy-19,20-dinor-prostanoate |
| 79 | 60 | Methyl 9-oxo-15-hydroxy-19,20-dinor-prostanoate |
| 80 | 61 | Decyl 9-oxo-15-hydroxy-19,20-dinor-prostanoate |
| 81 | 62 | Ethyl 9-oxo-15-hydroxy-5,6,7-trinor-prostanoate |
| 82 | 63 | Ethyl 9-oxo-15-hydroxy-6,7-dinor-prostanoate |
| 83 | 64 | Ethyl 9-oxo-15-hydroxy-7a,7b-bishomo-prostanoate |
| 84 | 65 | Ethyl 9-oxo-15-hydroxy-7-nor-prostanoate |
| 85 | 66 | Ethyl 9-oxo-15-hydroxy-7a-homo-prostanoate |
| 86 | 67 | Butyl 9-oxo-15-hydroxy-prostanoate |
| 87 | 68 | Isopropyl 9-oxo-15-hydroxy-prostanoate |
| 88 | 69 | Methyl 9-oxo-15-hydroxy-prostanoate |
| 89 | 70 | Decyl 9-oxo-15-hydroxy-prostanoate |

EXAMPLE 90

Preparation of ethyl 15-methanesulfonyloxy-9-oxo-prostanoate

To a stirred solution of 2.48 g. of ethyl 15-hydroxy-9-oxo-prostanoate (Example 50) in 18 ml. of methylene chloride containing 1.4 ml. of triethylamine, cooled in an ice-salt bath is added dropwise 0.58 ml. of methanesulfonyl chloride. The resulting mixture is stirred for 15 minutes and is then washed successively with ice cold water, 10% hydrochloric acid, saturated sodium bicarbonate solution, and saturated sodium chloride solution, dried with anhydrous magnesium sulfate and taken to dryness to give 2.7 g. (90%) of oil; λmax. 5.78 (carbonyl groups), 7.45 and 8.55 μ (sulfonate).

EXAMPLES 91-109

Treatment of the various 15-hydroxyprostanoates listed in Table 4 below with methylenesulfonyl chloride in accordance with the procedure of Example 90 above is productive of the 15-methanesulfonyloxyprostanate of the table.

TABLE 4

| Ex. | Starting 15-hydroxyprostanoate of example | Product 9-oxo-15-methanesulfonyloxy-prostanoate |
|---|---|---|
| 91 | 71 | Ethyl 9-oxo-15-methane-sulfonyloxy-19,20-dinor-prostanoate |
| 92 | 72 | Ethyl 9-oxo-15-methane-sulfonyloxy-5,6,7,19,20-pentanor-prostanoate |
| 93 | 73 | Ethyl 9-oxo-15-methane-sulfonyloxy-6,7,19,20-tetranor-prostanoate |
| 94 | 74 | Ethyl 9-oxo-15-methane-sulfonyloxy-7a,7b-bishomo-19,20-dinor-prostanoate |
| 95 | 75 | Ethyl 9-oxo-15-methane-sulfonyloxy-7,19,20-trinor-prostanoate |
| 96 | 76 | Ethyl 9-oxo-15-methane-sulfonyloxy-7a-homo-19,20-dinor-prostanoate |
| 97 | 77 | Butyl 9-oxo-15-methane-sulfonyloxy-19,20-dinor-prostanoate |
| 98 | 78 | Isopropyl-9-oxo-15-methane-sulfonyloxy-19,20-dinor-prostanoate |
| 99 | 79 | Methyl 9-oxo-15-methane-sulfonyloxy-19,20-dinor-prostanoate |
| 100 | 80 | Decyl 9-oxo-15-methane-sulfonyloxy-19,20-dinor-prostanoate |
| 101 | 81 | Ethyl 9-oxo-15-methane-sulfonyloxy-5,6,7,-trinor-prostanoate |
| 102 | 82 | Ethyl 9-oxo-15-methane-sulfonyloxy-6,7-dinor-prostanoate |
| 103 | 83 | Ethyl 9-oxo-15-methane-sulfonyloxy-7a,7b-bishomo-prostanoate |
| 104 | 84 | Ethyl 9-oxo-15-methane-sulfonyloxy-7-nor-prostanoate |

TABLE 4-continued

| Ex. | Starting 15-hydroxyprostanoate of example | Product 9-oxo-15-methanesulfonyloxy-prostanoate |
|---|---|---|
| 105 | 85 | Ethyl 9-oxo-15-methane-sulfonyloxy-7a-homo-prostanoate |
| 106 | 86 | Butyl 9-oxo-15-methane-sulfonyloxy-prostanoate |
| 107 | 87 | Isopropyl 9-oxo-15-methane-sulfonyloxy-prostanoate |
| 108 | 88 | Methyl 9-oxo-15-methane-sulfonyloxy-prostanoate |
| 109 | 89 | Decyl 9-oxo-15-methane-sulfonyloxy-prostanoate |

EXAMPLE 110

Preparation of ethyl 15-azido-9-oxo-prostanoate

A solution of 1.35 g. of ethyl 15-methanesulfonyloxy 9-oxo-prostanoate (Example 90) in 60 ml. of N,N-dimethylformamide containing 1.25 g. of sodium azide is heated on the steam-bath for 18 hours. The cooled solution is poured into 300 ml. of water and the resulting mixture is extracted several times with ether. The combined ether extracts are washed with saturated sodium chloride solution, dried with anhydrous magnesium sulfate and taken to dryness. The residual oil is chromatographed on silica gel to give 737 mg. (62%) of oil; $\lambda$max. 4.77 1 (azido) and 5.78 $\mu$ (carbonyl groups).

EXAMPLE 111

Preparation of ethyl 15-chloro-9-oxo-prostanoate

A solution of 1.35 g. of ethyl 15-methanesulfonyloxy 9-oxo-prostanoate (Example 90) in 40 ml. of N,N-dimethylformamide containing 650 mg. of lithium chloride is heated on the steam bath for 18 hours. The cooled solution is diluted with water and the resulting mixture is extracted with ether. The ether extract is washed with saline, dried with saline, dried with anhydrous magnesium sulfate and evaporated to dryness to give an oil. Chromatography on silica gel affords an oil; $\lambda$ max. 5.78 $\mu$ (carbonyl groups).

EXAMPLE 112

Preparation of ethyl 9-oxo-15-thiocyano-prostanoate

A solution of 1 g. of ethyl 15-methanesulfonyloxy-9-oxo-prostanoate (Example 90) and 1 g. of dry potassium thiocyanante in 30 ml. of N,N-dimethylformamide is heated on the steam bath for 18 hours. The resulting mixture is poured into 150 ml. of water and extracted with ether. The extract is washed with water, dried with anhydrous magnesium sulfate and taken to dryness. Silica gel chromatography of the residue gives 462 mg. of oil; $\lambda$ max. 4.67 (thiocyanate group) and 5.78 $\mu$ (carbonyl groups).

EXAMPLE 113

Preparation of ethyl 15-acetylthio-9-oxo-prostanoate

A solution of 1 g. of ethyl 15-methanesulfonyloxy-9-oxo-prostanoate (Example 90) in 50 ml. of acetone containing 735 mg. of purified potassium thiolacetate is kept at the reflux temperature for 2 hours, then at room temperature for 18 hours. The mixture is diluted with water and the resulting solution is washed with saturated sodium chloride solution, dried with magnesium sulfate and taken to dryness. The residue is chromatographed on silica gel to give an oil;

$\lambda$ max. 5.78 (ring carbonyl and ester group) and 5.92 $\mu$ (acetylthio group).

EXAMPLE 114-142

Treatment of the 15-methanesulfonyloxyprostanoates listed in Table 5 below with the indicated reagent, by the methods describing examples 110 (for sodium azide), 111 (for lithium chloride), 112 (for potassium thiolacetate) or 113 (for potassium thiolacetate) is productive of the 15-substituted prostanoates of the Table.

TABLE 5

| Ex. | Starting 15-methane-sulfonyloxy prostanoates of example | Reagent | Product 9-oxo-15-substituted-prostanoate |
|---|---|---|---|
| 114 | 91 | NaN$_3$ | Ethyl 9-oxo-15-azido-19,20-dinor-prostanoate |
| 115 | 94 | NaN$_3$ | Ethyl 9-oxo-15-azido-7a,7b-bishomo-19,20-dinor-prostanoate |
| 116 | 95 | NaN$_3$ | Ethyl 9-oxo-15-azido-7,19,20-trinor-prostanoate |
| 117 | 100 | NaN$_3$ | Decyl 9-oxo-15-azido-19,20-dinor-prostanoate |
| 118 | 102 | NaN$_3$ | Ethyl 9-oxo-15-azido-6,7-dinor-prostanoate |
| 119 | 103 | NaN$_3$ | Ethyl 9-oxo-15-azido-7a,7b-bishomo-prostanoate |
| 120 | 104 | NaN$_3$ | Ethyl 9-oxo-15-azido-7-nor-prostanoate |
| 121 | 105 | NaN$_3$ | Ethyl 9-oxo-15-azido-7a-homo-prostanoate |
| 122 | 106 | NaN$_3$ | Butyl 9-oxo-15-azido-prostanoate |
| 123 | 91 | CH$_3$C(=O)SK | Ethyl 9-oxo-15-acetylthio-19,20-dinor-prostanoate |
| 124 | 92 | " | Ethyl 9-oxo-15-acetylthio-5,6,7,19,20-pentanor-prostanoate |
| 125 | 96 | " | Ethyl 9-oxo-15-acetylthio-7a-homo-19,20-dinor-prostanoate |
| 126 | 99 | " | Methyl 9-oxo-15-acetylthio-19,20-dinor-prostanoate |
| 127 | 104 | " | Ethyl 9-oxo-15-acetylthio-7-nor-prostanoate |
| 128 | 105 | " | Ethyl 9-oxo-15-acetylthio-7-homo-prostanoate |
| 129 | 108 | " | Methyl 9-oxo-15-acetylthio-prostanoate |
| 130 | 91 | LiCl | Ethyl 9-oxo-15-chloro-19,20-dinor-prostanoate |
| 131 | 99 | LiCl | Methyl-9-oxo-15-chloro-19,20-dinor-prostanoate |
| 132 | 93 | LiCl | Ethyl -9-oxo-15-chloro-6,7,19,20-tetranor-prostanoate |
| 133 | 97 | LiCl | Butyl 9-oxo-15-chloro-19,20-dinor-prostanoate |
| 134 | 102 | LiCl | Ethyl 9-oxo-15-chloro-6,7-dinor-prostanoate |
| 135 | 108 | LiCl | Methyl 9-oxo-15-chloro-prostanoate |
| 136 | 105 | LiCl | Ethyl 9-oxo-15-chloro-7a-homo-prostanoate |
| 137 | 98 | KCNS | Isopropyl 9-oxo-15-thiocyano-19,20-dinor-prostanoate |
| 137 | | | |
| 138 | 101 | KCNS | Ethyl 9-oxo-15-thiocyano-5,6,7-trinor- |

TABLE 5-continued

| Ex. | Starting 15-methane-sulfonyloxy prostanoates of example | Reagent | Product 9-oxo-15-substituted-prostanoate |
|---|---|---|---|
| 139 | 103 | KCNS | Ethyl 9-oxo-15-thiocyano-7a,7b-bishomo-prostanoate |
| 140 | 95 | KCNS | Ethyl 9-oxo-15-thiocyano-7,19,20-trinor-prostanoate |
| 141 | 107 | NaN$_3$ | Isopropyl 9-oxo-15-azido-prostanoate |
| 142 | 109 | NaN$_3$ | Decyl 9-oxo-15-azido-prostanoate |

EXAMPLE 143

Preparation of ethyl 15-amino-9-oxo-prostanoate

A 1.06 g. sample of ethyl 15-azido-9-oxo-prostanoate (Example 110) is hydrogenated using 100 mg. of 5% palladium on carbon in 50 ml. absolute alcohol for 16 hours. The filtration of the catalyst and evaporation of the solvent affords an oil. Silica gel chromatography gives 604 mg. of oil; λ max. 2.95, 6.30 (brucine) and 5.72 μ (carbonyl groups).

EXAMPLES 144–154

Hydrogenation of the various 15-azidoprostanoates listed in Table 6 below by the method described in Example 143 provides the 15-amino-prostanoates of the Table.

TABLE 6

| Ex. | Starting 15-azido prostanoate of Example | Product 9-oxo-15-amino-prostanoate |
|---|---|---|
| 144 | 114 | Ethyl 9-oxo-15-amino-19,20-dinor-prostanoate |
| 145 | 115 | Ethyl 9-oxo-15-amino-7a,7b-bishomo-19,20-dinor-prostanoate |
| 146 | 116 | Ethyl 9-oxo-15-amino-7,19,20-trinor-prostanoate |
| 147 | 117 | Decyl 9-oxo-15-amino-19,20-dinor-prostanoate |
| 148 | 118 | Ethyl 9-oxo-15-amino-6,7-dinor-prostanoate |
| 149 | 119 | Ethyl 9-oxo-15-amino-7a,7b-bishomo-prostanoate |
| 150 | 120 | Ethyl 9-oxo-15-amino-7-nor-prostanoate |
| 151 | 121 | Ethyl 9-oxo-15-amino-7a-homo-prostanoate |
| 152 | 122 | Butyl 9-oxo-15-amino-prostanoate |
| 153 | 141 | Isopropyl 9-oxo-15-amino-prostanoate |
| 154 | 142 | Decyl 9-oxo-15-amino-prostanoate |

EXAMPLE 155

Preparation of ethyl 9-oxo-15-mercapto-prostanoate

A solution of 606 mg. of ethyl 15-acetylthio-9-oxo-prostanoate (Example 113) in 20 ml. of reagent methanol is treated, under nitrogen atmosphere, with 1.6 ml. of 1N methanolic sodium methoxide. After 10 minutes the reaction is quenched by the addition of 0.3 ml. of glacial acetic acid and taken to dryness. A solution of the residue in ether is washed with saturated sodium chloride solution, dried with anhydrous magnesium sulfate and taken to dryness to afford 428 mg. (89%) of an oil; λ max. 4.0 (sulfhydryl) and 5.78 μ (carbonyls).

EXAMPLES 156–162

Brief treatment of the various 15-acetylthio-prostanoates listed in Table 7 below with methanolic methoxide by the method described in Example 155 immediately preceding is productive of the 15-mercapto-prostanoates of the Table.

TABLE 7

| Ex. | Starting 15-acetyl-thio-prostenoate of Example | Product 9-oxo-15-mercapto-prostanoate |
|---|---|---|
| 156 | 123 | Ethyl 9-oxo-15-mercapto-19,20-dinor-prostanoate |
| 157 | 124 | Ethyl 9-oxo-15-mercapto-5,6,7,19,20-pentanor-prostanoate |
| 158 | 125 | Ethyl 9-oxo-15-mercapto-7a-homo-19,20-dinor-prostanoate |
| 159 | 126 | Methyl 9-oxo-15-mercapto-19,20-dinor-prostanoate |
| 160 | 127 | Ethyl 9-oxo-15-mercapto-7-nor-prostanoate |
| 161 | 128 | Ethyl 9-oxo-15-mercapto-7-homo-prostanoate |
| 162 | 129 | Methyl 9-oxo-15-mercapto-prostanoate |

EXAMPLE 163

Preparation of 15-azido-9-oxo-prostanoic acid

A suspension of 880 mg. of ethyl 15-azido-9-oxo-prostanoate (Example 110) in 15 ml. of methanol-water (1:1) containing 360 mg. of potassium hydroxide is stirred at ambient temperature for 18 hours. The resulting solution is acidified with dilute hydrochloric acid and the oily layer is taken up in ether. The ether is washed with saturated sodi sodium chloride solution, dried with anhydrous magnesium sulfate and taken to dryness to give 797 mg. (98%) of an oil;

λ max. 3.0–3.5 broad (acid group), 4.88 (azido group), 5.78 and 5.90 (carbonyl groups).

EXAMPLES 164–175

Saponification of the various prostanoic esters listed in Table 8 below is productive of the corresponding acids listed in the table

TABLE 8

| Ex. | Starting prostanoate ester of Example | Product 15-substituted-9-oxo-prostanoic acid |
|---|---|---|
| 164 | 114 | 9-oxo-15-azido-19,20-dinor-prostanoic acid |
| 165 | 115 | 9-oxo-15-azido-7a,7b-bishomo-19,20-dinor-prostanoic acid |
| 166 | 116 | 9-oxo-15-azido-7,19,20-trinor-prostanoic acid |
| 167 | 118 | 9-oxo-15-azido-6,7-dinor-prostanoic acid |
| 168 | 119 | 9-oxo-15-azido-7a,7b-bishomo-prostanoic acid |
| 169 | 120 | 9-oxo-15-azido-7-nor-prostanoic acid |
| 170 | 121 | 9-oxo-15-azido-7a-homo-prostanoic acid |
| 171 | 123 | 9-oxo-15-mercapto-19,20-dinor-prostanoic acid |
| 172 | 128 | 9-oxo-15-mercapto-7-homo-prostanoic acid |
| 173 | 129 | 9-oxo-15-mercapto-prostanoic acid |
| 174 | 131 | 9-oxo-15-chloro-19,20-dinar-prostanoic acid |
| 175 | 135 | 9-oxo-15-chloro-prostanoic |

TABLE 8-continued

| Ex. | Starting prostanoate ester of Example | Product 15-substituted-9-oxo-prostanoic acid |
|---|---|---|
| 176 | 71 | 9-oxo-15-hydroxy-19,20-dinor-prostanoic acid |
| 177 | 72 | 9-oxo-15-hydroxy-5,6,7,19,20-pentanor-prostanoic acid |
| 178 | 73 | 9-oxo-15-hydroxy-6,7,19,20-tetranor-prostanoic acid |
| 179 | 74 | 9-oxo-15-hydroxy-7a,7b-bishomo-19,20-dinor-prostanoic acid |
| 180 | 75 | 9-oxo-15-hydroxy-7,19,20-trinor-prostanoic acid |
| 181 | 76 | 9-oxo-15-hydroxy-7a-homo-19,20-dinor-prostanoic acid |
| 182 | 81 | 9-oxo-15-hydroxy-5,6,7-trinor-prostanoic acid |
| 183 | 82 | 9-oxo-15-hydroxy-6,7-dinor-prostanoic acid |
| 184 | 83 | 9-oxo-15-hydroxy-7a,7b-bis-homo-prostanoic acid |
| 185 | 84 | 9-oxo-15-hydroxy-7-nor-prostanoic acid |
| 186 | 50 | 9-oxo-15-hydroxy-prostanoic acid |

EXAMPLE 187

Preparation of 9α,15-dihydroxyprostanoic acid

To a solution of 433 mg. of 15-hydroxy-9-oxoprostanoic acid (Example 186) in 4.5 ml. of tetrahydrofuran, stirred in an ice-bath under nitrogen atmosphere, is added dropwise 3.7 ml. of 0.76 M lithium perhydro-9b-boraphenalylhydride. After 40 minutes at 0° C. there is added 1.62 ml. of 3N sodium hydroxide followed by 1.62 ml. of 30% hydrogen peroxide. Ether is added and the resulting solution is acidified with 2N hydrochloric acid. The ether layer is washed several times with saturated sodium chloride solution, dried with anhydrous magnesium sulfate and taken to dryness to give 300 mg. (70%) of waxy solid; nmr 3H singlet δ 4.64 (hydroxyl and carboxyl protons), 1 H singlet 4.22 (9β-carbinolic proton, 80%), 1 H singlet 3.88 (9α-carbinolic protons, 20%), 1 H singlet 3.61 (15-carbinolic proton), and 3 H distorted triplet 0.90 (terminal methyl).

EXAMPLES 188–203

Treatment of the various 9-oxoprostanoic acids listed in Table 9 below with lithium perhydro-9b-boraphenalyl hydride by the procedure described in Example 187 is productive of the 9α-hydroxy derivatives of the table.

TABLE 9

| Ex. | Starting 9-oxo-prostanoic acid of Example | Product 9α-hydroxy-prostanoic acids |
|---|---|---|
| 188 | 163 | 9α-hydroxy-15-azido-prostanoic acid |
| 189 | 171 | 9α-hydroxy-15-mercapto-19,20-dinor-prostanoic acid |
| 190 | 173 | 9α-hydroxy-15-mercapto-prostanoic acid |
| 191 | 174 | 9α-hydroxy-15-chloro-19,20-dinor-prostanoic acid |
| 192 | 175 | 9α-hydroxy-15-chloro-prostanoic acid |
| 193 | 176 | 9α,15-dihydroxy-19,20-dinor-prostanoic acid |
| 194 | 177 | 9α,15-dihydroxy-5,6,7,19,20-pentanor-prostanoic acid |
| 195 | 178 | 9α,15-dihydroxy-6,7,19,20-tetranor-prostanoic acid |
| 196 | 179 | 9α,15-dihydroxy-7a,7b-bishomo-19,20-dinor-prostanoic acid |
| 197 | 180 | 9α,15-dihydroxy-7,19,20-trinor-prostanoic acid |
| 198 | 181 | 9α,15-dihydroxy-7a-homo-19,20-dinor-prostanoic acid |
| 199 | 182 | 9α,15-dihydroxy-5,6,7-trinor-prostanoic acid |
| 200 | 183 | 9α,15-dihydroxy-6,7-dinor-prostanoic acid |
| 201 | 184 | 9α,15-dihydroxy-7a,7b-bishomo-prostanoic acid |
| 202 | 185 | 9α,15-dihydroxy-7-nor-prostanoic acid |
| 203 | 186 | 9α,15-dihydroxy-7a-homo-prostanoic acid |

EXAMPLE 204

Preparation of ethyl 9α,15-dihydroxyprostanoate ethyl ester

Treatment of 15-hydroxy-9-oxoprostanoic acid, ethyl ester in tetrahydrofuran with 0.76M lithium perhydro-9b-boraphenalylhydride according to the procedure described in Example 187 gives an oily product; λ max. 2.90, 5.75, 8.45 μ.

EXAMPLE 205–246

Treatment of the 9-oxo- prostanoate esters of Table 10 below with lithium perhydro-9b-boraphenalyl hydride by the procedure of Example 204 is productive of the 9α-hydroxy-prostanoates of the table.

TABLE 10

| Ex. | Starting 9-oxo-prostanoate of Example | Product 9α-hydroxy-prostanoate |
|---|---|---|
| 205 | 71 | Ethyl 9α,15-dihydroxy-19,20-dinor-prostanoate |
| 206 | 72 | Ethyl 9α,15-dihydroxy-5,6,7,19,20-pentanor-prostanoate |
| 207 | 73 | Ethyl 9α,15-dihydroxy-6,7,19,20-tetranor-prostanoate |
| 208 | 74 | Ethyl 9α,15-dihydroxy-7a,7b-bishomo-19,20-dinor-prostanoate |
| 209 | 75 | Ethyl 9α,15-dihydroxy-7,19,20-trinor-prostanoate |
| 210 | 76 | Ethyl 9α,15-dihydroxy-7a-homo-19,20-dinor-prostanoate |
| 211 | 77 | Butyl 9α,15-dihydroxy-19,20-dinor-prostanoate |
| 212 | 78 | Isopropyl 9α,15-dihydroxy-19,20-dinor-prostanoate |
| 213 | 79 | Methyl 9α,15-dihydroxy-19,20-dinor-prostanoate |
| 214 | 80 | Decyl 9α,15-dihydroxy-19,20-dinor-prostanoate |
| 215 | 81 | Ethyl 9α,15-dihydroxy-5,6,7,-trinor-prostanoate |
| 216 | 82 | Ethyl 9α,15-dihydroxy-6,7-dinor-prostanoate |
| 217 | 83 | Ethyl 9α,15-dihydroxy-7a,7b-bishomo-prostanoate |
| 218 | 84 | Ethyl 9α,15-dihydroxy-7-nor-prostanoate |
| 219 | 85 | Ethyl 9α,15-dihydroxy-7a-homo-prostanoate |
| 220 | 86 | Butyl 9α,15-dihydroxy-prostanoate |
| 221 | 87 | Isopropyl 9α,15-dihydroxy-prostanoate |
| 222 | 88 | Methyl 9α,15-dihydroxy-prostanoate |
| 224 | 110 | Ethyl 9α-hydroxy-15-azido-prostanoate |
| 225 | 111 | Ethyl 9α-hydroxy-15-chloro-prostanoate |
| 226 | 142 | Decyl 9α-hydroxy-15-azido-prostanoate |
| 227 | 143 | Ethyl 9α-hydroxy-15-amino-prostanoate |
| 228 | 144 | Ethyl 9α-hydroxy-15-amino-19,20-dinor-prostanoate |
| 229 | 145 | Ethyl 9α-hydroxy-15-amino-7a,7b-bishomo-19,20-dinor-prostanoate |

TABLE 10-continued

| Ex. | Starting 9-oxo-prostanoate of Example | Product 9α-hydroxy-prostanoate |
|---|---|---|
| 230 | 146 | Ethyl 9α-hydroxy-15-amino-7,19,20-trinor-prostanoate |
| 231 | 147 | Decyl 9α-hydroxy-15-amino-19,20-dinor-prostanoate |
| 232 | 148 | Ethyl 9α-hydroxy-15-amino-6,7-dinor-prostanoate |
| 233 | 149 | Ethyl 9α-hydroxy-15-amino-7a,7b-bishomo-prostanoate |
| 234 | 150 | Ethyl 9α-hydroxy-15-amino-7-nor-prostanoate |
| 235 | 151 | Ethyl 9α-hydroxy-15-amino-7a-homo-prostanoate |
| 236 | 152 | Butyl 9α-hydroxy-15-amino-prostanoate |
| 237 | 153 | Isopropyl-9α-hydroxy-15-amino-prostanoate |
| 238 | 154 | Decyl 9α-hydroxy-15-amino-prostanoate |
| 239 | 155 | Ethyl 9α-hydroxy-15-mercapto-prostanoate |
| 240 | 156 | Ethyl 9α-hydroxy-15-mercapto-19,20-dinor-prostanoate |
| 241 | 157 | Ethyl 9α-hydroxy-15-mercapto-5,6,7,19,20-pentanor-prostanoate |
| 242 | 158 | Ethyl 9α-hydroxy-15-mercapto-7a-homo-19,20-dinor-prostanoate |
| 243 | 159 | Methyl 9α-hydroxy-15-mercapto-19,20-dinor-prostanoate |
| 244 | 160 | Ethyl 9α-hydroxy-15-mercapto-7-nor-prostanoate |
| 245 | 161 | Ethyl 9α-hydroxy-15-mercapto-7-homo-prostanoate |
| 246 | 162 | Methyl 9α-hydroxy-15-mercapto-prostanoate |

EXAMPLE 247

Preparation of ethyl 9α/β,15-dihydroxyprostanoate

A solution of 3 g. of ethyl 15-hydroxy-9-oxo-prostanoate (Example 50), in 120 ml. of absolute alcohol containing 115 mg. of sodium borohydride is stirred at ambient temperature for 18 hours. The solution is poured into 300 ml. of saturated sodium chloride solution and the oily precipitate is extracted with ether. The ether phase is washed with saturated sodium chloride solution, dried with anhydrous magnesium sulfate and taken to dryness to give 2.74 g. of an oil; λ max. 2.95, 5.78, 8.45 μ; the product is a mixture of 9α- and 9β-hydroxy derivatives.

EXAMPLES 248-251

Treatment of the 9-oxo-prostanoates listed in Table 11 below with sodium borohydride by the procedure described in Example 247 is productive of the mixture of 9α- and 9β-hydroxy-prostanoates of the Table.

TABLE 11

| Ex. | Starting 9-oxo-prostanoate of Example | Product 9α/9β-hydroxy-prostanoate |
|---|---|---|
| 248 | 110 | Ethyl 9α/9β-hydroxy-15-azido-prostanoate |
| 249 | 111 | Ethyl 9α/9β-hydroxy-15-chloro-prostanoate |
| 250 | 143 | Ethyl 9α/9β-hydroxy-15-amino-prostanoate |
| 251 | 155 | Ethyl 9α/9β-hydroxy-15-mercapto-prostanoate |

EXAMPLES 252-254

Saponification of the 9α/9β-hydroxy prostanoates of Table 12 below by the method described in Example 163 is productive of the prostanoic acids of the Table.

TABLE 12

| Ex. | Starting prostanoates of Example | Product 9α/9β-hydroxy-prostanoic acid |
|---|---|---|
| 252 | 248 | 9α/9β-hydroxy-15-azido-prostanoic acid |
| 253 | 249 | 9α/9β-hydroxy-15-chloro-prostanoic acid |
| 254 | 251 | 9α/9β-hydroxy-15-mercapto-prostanoic acid |

EXAMPLE 255

Preparation of 15-amino-9-oxoprostanoic acid hydrochloride

A solution of 1 g. of ethyl 15-amino-9-oxo-prostanoate (Example 143) in 15 ml. of methanol-water (1:1) containing 445 mg. of potassium hydroxide is stirred at ambient temperature for 18 hours. The solution is acidified with hydrochloric acid, saturated with sodium chloride, and extracted several times with methylene chloride. The organic phase is dried with anhydrous magnesium sulfate and taken to dryness to give a viscous oil; λ max. 2.80 – 3.70 (broad), 5.75, and 5.87 μ.

EXAMPLES 256-271

Ester hydrolysis of the 15-amino-prostanoates listed in Table 13 below by the procedure described in Example 255 is productive of the 15-amino-prostanoic acid hydrochlorides of the Table.

TABLE 13

| Ex. | Starting 15-amino-prostanoate of Example | Product 15-amino-prostanoic acid hydrochloride |
|---|---|---|
| 256 | 144 | 9-oxo-15-amino-19,20-dinor-prostanoic acid . HCl |
| 257 | 145 | 9-oxo-15-amino-7a,7b-bis-homo-19,20-dinor-prostanoic acid . HCl |
| 258 | 146 | 9-oxo-15-amino-7,19,20-trinor-prostanoic acid . HCl |
| 259 | 148 | 9-oxo-15-amino-6,7-dinor-prostanoic acid . HCl |
| 260 | 149 | 9-oxo-15-amino-7a,7b-bishomo-prostanoic acid . HCl |
| 261 | 150 | 9-oxo-15-amino-7-nor-prostanoic acid . HCl |
| 262 | 151 | 9-oxo-15-amino-7a-homo-prostanoic acid . HCl |
| 263 | 227 | 9α-hydroxy-15-amino-prostanoic acid . HCl |
| 264 | 228 | 9α-hydroxy-15-amino-19,20-dinor-prostanoic acid . HCl |
| 265 | 229 | 9α-hydroxy-15-amino-7a,7b-bishomo-19,20-dinor-prostanoic acid . HCl |
| 266 | 230 | 9α-hydroxy-15-amino-7,19,20-trinor-prostanoic acid . HCl |
| 267 | 232 | 9α-hydroxy-15-amino-6,7-dinor-prostanoic acid . HCl |
| 268 | 233 | 9α-hydroxy-15-amino-7a,7b-bishomo-prostanoic acid . HCl |
| 269 | 234 | 9α-hydroxy-15-amino-7-nor-prostanoic acid . HCl |
| 270 | 235 | 9α-hydroxy-15-amino-7a-homo-prostanoic acid |
| 271 | 250 | 9α/9β-hydroxy-15-amino-prostanoic acid . HCl |

EXAMPLE 272

Preparation of 9β,15-dihydroprostanoic acid

A solution of ethyl 9β,15-dihydroxyprostanoate in 32 ml. of methanol-water (1:1), containing 890 mg. of potassium hydroxide is kept at ambient temperature for 18 hours. The solution is acidified with dilute hydrochloric acid and extracted several times with ether. The ether phase is washed with saturated sodium chloride solution, dried with anhydrous magnesium sulfate and taken to dryness to give 1.63 g. of an oil; nmr 3H singlet δ 5.53 (hydroxyl and carboxyl protons), 1H singlet 4.23 (9β-carbinolic proton, 30%), 1H singlet 3.90 (9α-carbinolic proton, 70%), 1H singlet 3.65 (15-carbinolic proton), and 3H distorted triplet 0.90 (terminal methyl).

EXAMPLE 273

Preparation of methyl 1-15(S)-acetoxy-9-oxo-prostanoate

A solution of 2.5 g. of methyl 15(S)-acetoxy-9-oxo-5-cis, 10,13-trans-prostatrienoate [W. P. Schneider, R. D. Hamilton, L. E. Rhuland, Jour. Amer. Chem. Soc., 94, 2122 (1972)] in 150 ml. of ethyl acetate is hydrogenated using 5% rhodium-on-carbon catalyst. Removal of the catalyst by filtration followed by evaporation of the solvent gives 2.26 g. of subject compound as an oil; λmax 5.80 (carbonyl groups).

EXAMPLE 274

Preparation of methyl 1-15(S)-hydroxy-9-oxo-prostanoate

A solution of 2.26 g. of methyl 15(S)-acetoxy-9-oxo-prostanoate (Example 15) in 300 ml. of absolute alcohol containing 790 mg. of potassium carbonate is stirred at ambient temperature for 72 hours then concentrated to near dryness under reduced pressure. The resulting mixture is extracted with ether. The combined extracts are washed with saturated sodium chloride solution, dried with anhydrous magnesium sulfate and taken to dryness to give 1.83 g. of an oil. Purification by silica gel chromatography affords the subject compound as an oil; λ max. 2.92 (hydroxyl group), 5.74 μ (carbonyl groups); $[\alpha]_D^{25} -23°$ C. (0.2% in CHCL$_3$).

EXAMPLE 275

Preparation of 1-15-(S)-hydroxy-9-oxo-prostanoic acid

A solution of 930 mg. of methyl 15(S)-hydroxy-9-oxo-prostanoate (Example 16) in 16 ml. of methanol-water (1:1) containing 410 mg. of potassium hydroxide is stirred at ambient temperature for 18 hours. The solution is acidified with 1N hydrochloric acid and extracted with ether. The ether extract is washed with saturated with saturated sodium chloride solution, dried with anhydrous magnesium sulfate and evaporated to dryness in vacuo to give 797 mg. of viscous oil; 2.94 –4.00 (broad) (hydroxyl and carboxyl groups), 5.80 (ketone carbonyl group), and 5.87 μ (acid carbonyl group); $[\alpha]_D^{25} -23°$ C. (0.6% in CHCl$_3$).

We claim:

1. A compound of the formula:

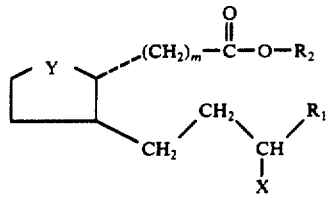

wherein $m$ is an integer from 5 to 8, inclusive; $R_1$ is an alkyl group having from 3 to 6 carbon atoms, inclusive; $R_2$ is selected from the group consisting of hydrogen and an alkyl group having up to 4 carbon atoms; X is selected from the group consisting of mercapto and lower alkanoylthio; and Y is a divalent radical selected from the group consisting of those of the formulae:

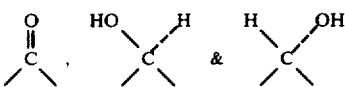

and the pharmaceutically acceptable cationic salts thereof when $R_2$ is hydrogen.

2. The racemic compound according to claim 1, dl-9-oxo-15-mercaptoprostanoic acid.

3. The racemic compound according to claim 1, dl-9-oxo-15-acetylthioprostanoic acid.

4. The racemic compound according to claim 1, dl-ethyl 9-oxo-15-acetylthioprostanoate.

5. The racemic compound according to claim 1, dl-ethyl 9-oxo-15-acetylthio-7-nor-prostanoate.

6. The racemic compound according to claim 1, dl-ethyl 9-oxo-15-acetylthio-7-homo-prostanoate.

7. The racemic compound according to claim 1, dl-ethyl 9-oxo-15-mercaptoprostanoate.

8. The racemic compound according to claim 1, dl-9-oxo-15-mercapto-7-homoprostanoic acid.

9. The racemic compound according to claim 1, dl-9α-hydroxy-15-mercaptoprostanoic acid.

10. The racemic compound according to claim 1, dl-ethyl 9α-hydroxy-15-mercaptoprostanoate.

11. The racemic compound according to claim 1, dl-ethyl 9-hydroxy-15-mercaptoprostanoate.

12. The racemic compound according to claim 1, dl-9-hydroxy-15-mercaptoprostanoic acid.

13. The racemic compound according to claim 1, dl-methyl-9α-15-mercaptoprostanoate.

14. The racemic compound according to claim 1, dl-methyl 9-oxo-15-mercaptoprostanoate.

15. The racemic compound according to claim 1, dl-ethyl 9-oxo-15-acetylthio-19,20-dinor-prostanoate.

16. The racemic compound according to claim 1, dl-methyl 9-oxo-15-acetylthio-prostanoate.

* * * * *